United States Patent
Zhang et al.

(10) Patent No.: US 6,532,799 B2
(45) Date of Patent: Mar. 18, 2003

(54) SYSTEM FOR IN-SITU AND ON-LINE MONITORING OF A PERFORM LAYUP PROCESS FOR LIQUID COMPOSITE MOLDING

(75) Inventors: Chun Zhang, Tallahassee, FL (US); Zhiyong Liang, Tallahassee, FL (US); Ben Wang, Tallahassee, FL (US); Chiang Shih, Tallahassee, FL (US)

(73) Assignee: Florida State University Research Foundation, Tallahassee, FL (US)

( * ) Notice: Subject to any disclaimer, the term of this patent is extended or adjusted under 35 U.S.C. 154(b) by 0 days.

(21) Appl. No.: 09/764,685

(22) Filed: Jan. 18, 2001

(65) Prior Publication Data

US 2002/0046596 A1 Apr. 25, 2002

Related U.S. Application Data

(60) Provisional application No. 60/176,326, filed on Jan. 18, 2000.

(51) Int. Cl.⁷ .................. G02N 15/08; B29C 45/76
(52) U.S. Cl. .................. 73/38; 425/144; 425/149; 264/40.1
(58) Field of Search .................. 73/38; 425/144, 425/149; 2641/40.1, 40.3

(56) References Cited

U.S. PATENT DOCUMENTS

| | | | |
|---|---|---|---|
| 3,590,634 A | * 7/1971 | Pasternak et al. | 374/54 |
| 3,762,211 A | 10/1973 | Poulsen | 73/38 |
| 3,808,876 A | 5/1974 | Kershaw | 73/38 |
| 3,865,561 A | * 2/1975 | Osborn | 356/439 |
| 4,064,740 A | 12/1977 | Crosby, Jr, | 73/38 |
| 4,660,411 A | * 4/1987 | Reid | 73/38 |
| 4,841,958 A | 6/1989 | Ersfeld et al. | 128/90 |
| 4,863,651 A | * 9/1989 | Koten | 264/328.1 |
| 5,558,824 A | 9/1996 | Shah et al. | 264/40.3 |
| 5,863,452 A | 1/1999 | Harshberger, Jr. et al. | 249/93 |
| 6,063,315 A | * 5/2000 | Keller et al. | 264/40.1 |
| 6,090,318 A | * 7/2000 | Bader et al. | 264/297.2 |

FOREIGN PATENT DOCUMENTS

| | | | |
|---|---|---|---|
| JP | 04288212 A | * | 10/1992 |
| JP | 10012649 A | * | 1/1998 |
| JP | 11320642 A | * | 11/1999 |

\* cited by examiner

*Primary Examiner*—Hezron Williams
*Assistant Examiner*—Michael Cygan
(74) *Attorney, Agent, or Firm*—Peter Loffler

(57) ABSTRACT

A system for in-situ and on-line monitoring of a preform layup process for liquid composite molding allows for gathering of permeability measurements of a fabric preform for use in a liquid composite molding process after situation of the preform within the mold wherein the molding process is to occur. The system uses a plurality of pressure sensors located within one of the mold sections of the liquid composite molding process mold. The sensors take pressure measurements which are processed to obtain a permeability profile of the preform. From such data, any local permeability variations that are caused from defects in the preform, deformation of the preform, or from mold misfit can be noted and acted upon before resin flow. The system is relatively simple to use and is easy to implement.

32 Claims, 10 Drawing Sheets

SYSTEM FOR IN-SITU AND ON-LINE MONITORING OF A PERFORM LAYUP PROCESS FOR LIQUID COMPOSITE MOLDING

This application claims the benefit of provisional patent application No. 60/176,326 filed on Jan. 18, 2000.

BACKGROUND OF THE INVENTION

1. Field of the Invention

The present invention relates to that gathers permeability measurements of a fabric preform for use in a liquid composite molding process after situation of the preform within the mold wherein the molding process is to occur.

2. Background of the Prior Art

Fiber reinforced composite materials are an important class of engineering materials that offer outstanding mechanical properties and unique design flexibility. Such materials are lightweight, corrosive resistant, impact resistant and exhibit excellent fatigue strength. Composite materials are used in a wide variety of applications including automotive parts, aviation, marine vessels, offshore structures, containers and piping, and sporting goods among others. Liquid composite molding, which includes resin transfer molding, reaction injection molding, and resin infusion, is one of the most attractive manufacturing solutions to producing high quality, affordable, and environmentally friendly composite materials.

Recently, a considerable amount of progress has been achieved for liquid composite molding techniques such as constituent material development, tooling, reinforcement preform development, curing control, and process simulation. These advances have lifted the liquid composite molding process to new heights.

However, a major barrier has retarded the advancement of liquid composite molding, the barrier being the reproducibility of the finished part, which tends to be lower than expected resulting in higher than expected manufacturing costs of the finished products actual manufactured and accepted.

In the liquid composite molding process, resin flow induced defects are recognized as the largest source of quality and reproducibility problems. The resin flow pattern is strongly related to fiber preform layup and mold fit. In a liquid composite molding process, poor raw material (fiber) quality or improper fiber preform preparation often result in local permeability variations. These permeability variations can lead to unbalanced resin flows, which in turn, produce defect parts.

Permeability, which characterizes the flow resistance of the fiber preform to the liquid resin in the liquid composite molding process, is widely used in liquid composite molding applications as one of the most important process design and control parameters. If serious permeability variations and misfit between the preform and the mold exist, defects will result in the resin low field, which leads to defective finished parts.

Current methods for testing the permeability of the preform use specially designed molds that measure the pressure and flow rate or flow distance of the resin to obtain an average permeability using Darcy's law. The problems for arriving at the permeability of the preform using the existing method are twofold. First, the method only delivers the average permeability of the preform. It does not measure local permeability variations of the fiber preform due to inherent raw material variations as well as improper preform loading. Second, the permeability measurements are conducted off-line. As the preform is a flexible structure, it is easy to deform and restructure during the handling process. When the preform is laid up in the production mold, significant changes in the preform permeability can be realized due to fiber deformation and mold misfit. Accordingly, the measured permeability may not represent the true value of the permeability of the preform in the production mold.

Therefore, there is a need in the art for a system for use in the liquid composite molding process that overcomes the above-stated problems in the art. Specifically, such a system must allow for a high level of reproducibility of the finished part manufactured using the liquid composite molding process. In order to achieve this high level, the permeability of the preform needs to be measured across the entire preform after situation of the preform within the actual mold wherein the liquid composite molding process upon the preform will occur so that preform fabric defects and/or mold misfits can be detected prior to the commencement of resin flow. Ideally, such a system will be of relatively simple construction and will be relatively easy to use and will not have adverse effects upon the finished product.

SUMMARY OF THE INVENTION

The system for in-situ and on-line monitoring of a preform layup process for liquid composite molding of the present invention addresses the aforementioned needs in the art. The system allows for gathering of permeability measurements of a fabric preform for use in a liquid composite molding process after situation of the preform within the mold wherein the molding process is to occur. The system can be used to create a pressure profile, a contour profile, or can be processed in any other fashion desired by the user. From such data, any local permeability measurements that are caused from defects in the preform, deformation of the preform, or from mold misfit can be noted and acted upon before resin flow. The system is relatively simple to use and is easy to implement.

The system for in-situ and on-line monitoring of a preform layup process for liquid composite molding of the present invention is comprised of a mold that has an upper section and a lower section forming a cavity therebetween and has an inlet port and an outlet port. A plurality of openings are located within the lower section while a plurality of pressure sensors are each attached to a respective one of the plurality of openings. A source of compressed gas is fluid flow connected to the inlet port. Each pressure sensor can be attached to its respective opening via an adapter which adapter can be operable between an open position wherein fluid flow communication between the pressure sensor and its respective opening is present and a closed position wherein fluid flow communication between the pressure sensor and its respective opening is absent. The pressure sensors may be MEMS pressure sensors. Each pressure sensor is connected to a data acquisition and processing device. which can be a computer. A reject hole located within the mold and a pin hole may each be located within the mold. A flow meter may be fluid flow connected with the inlet port, the flow meter also be connected to the data acquisition and processing device. A resin pump fluid flow is connected to the inlet port and may be fluid flow connected with the flow meter. The gas within the source of pressurized gas may be nitrogen.

BRIEF DESCRIPTION OF THE DRAWINGS

Similar reference numerals refer to similar parts throughout the several views of the drawings.

DESCRIPTION OF THE PREFERRED EMBODIMENT

Figure 1:
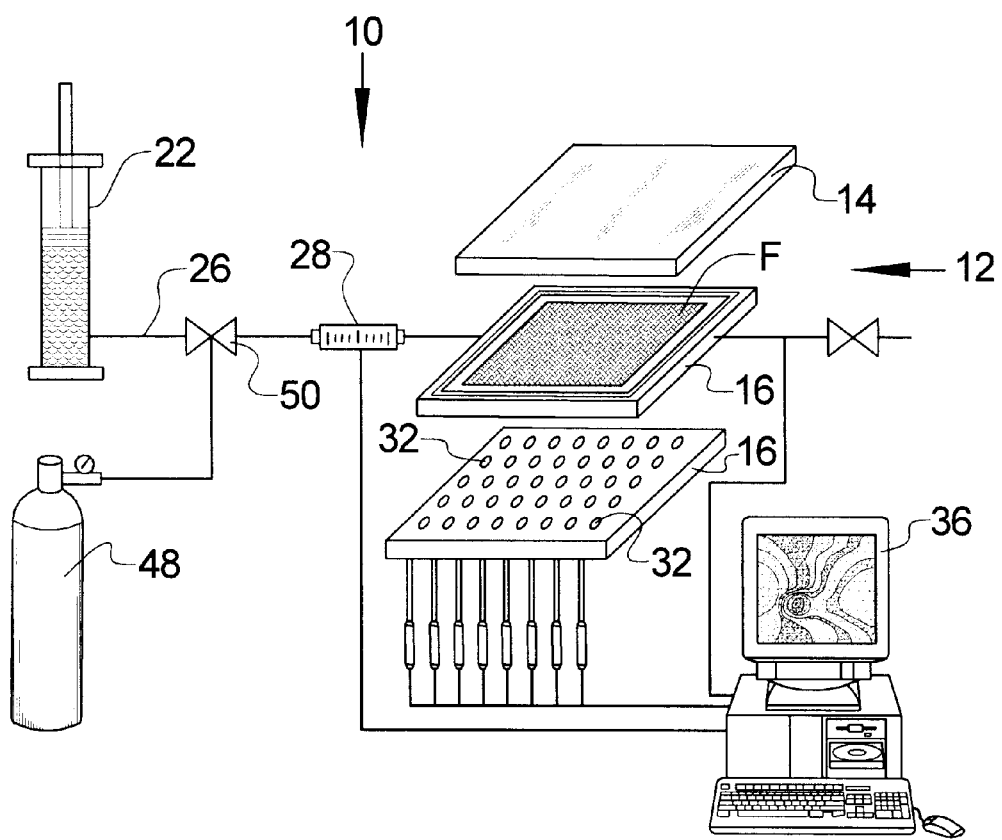
FIG. 1 is a perspective view of the system for in-situ and on-line monitoring of a preform layup process for liquid composite molding of the present invention.
Figure 2:
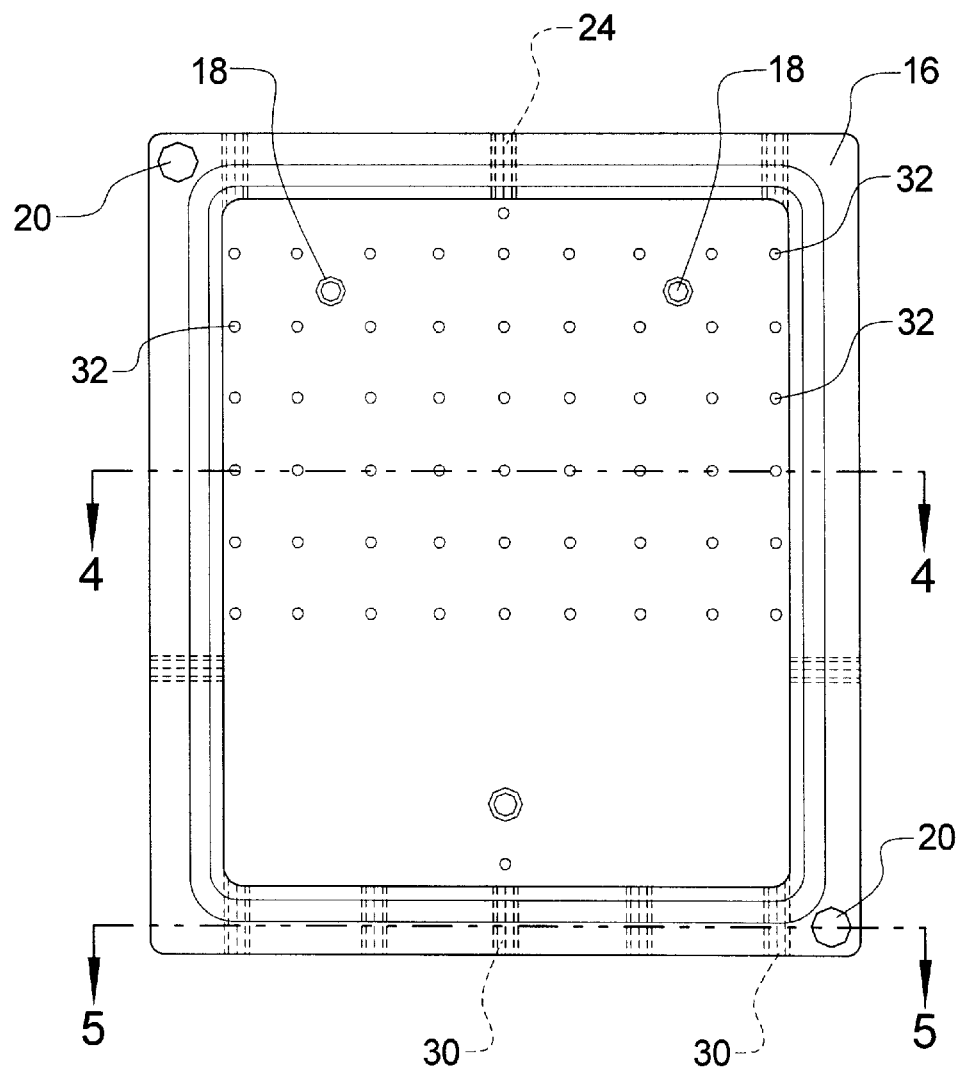
FIG. 2 is a top plan view of the lower mold section.
Figure 3:
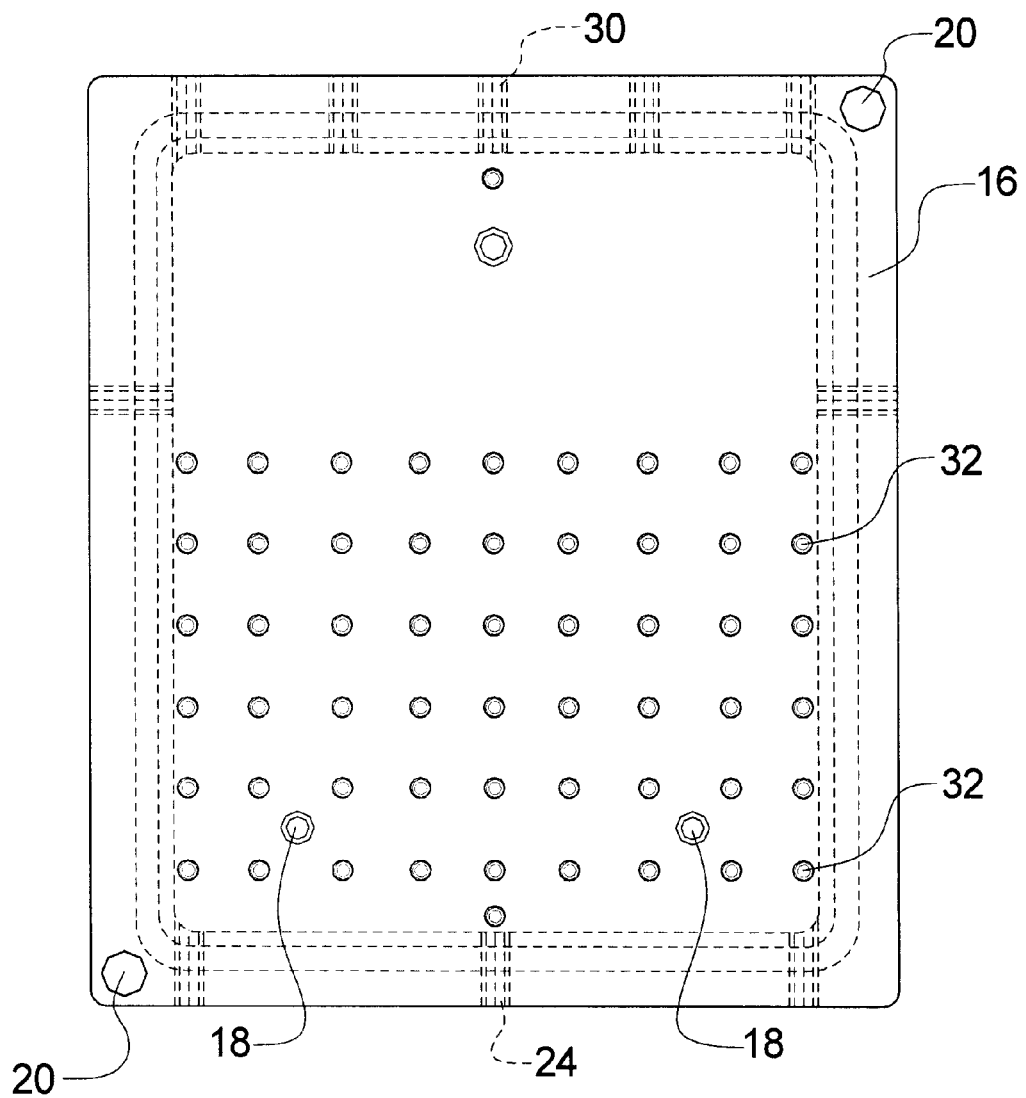
FIG. 3 is a bottom plan view of the lower mold section.
Figure 4:
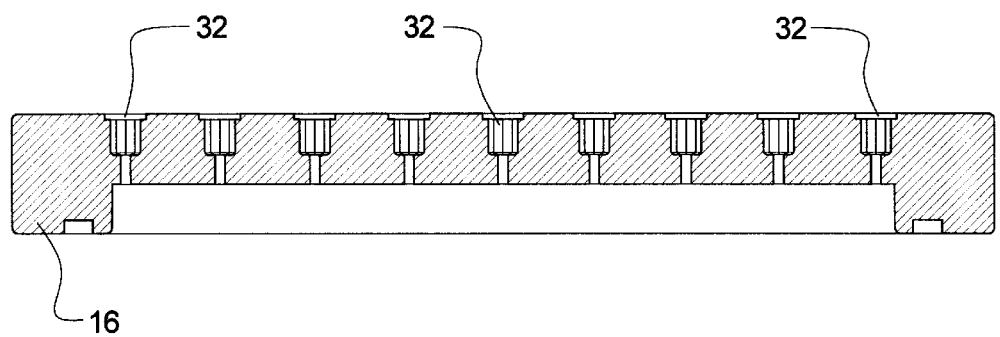
FIG. 4 is a sectioned view of the lower mold section taken along line 4—4 in FIG. 2.
Figure 5:
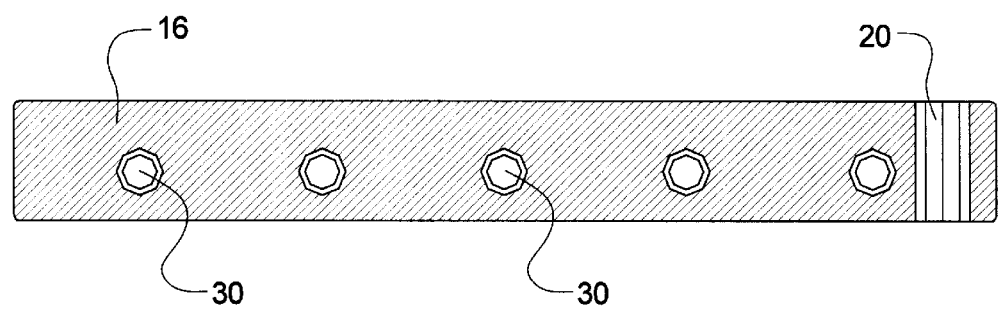
FIG. 5 is a sectioned view of the lower mold section taken along line 5—5 in FIG. 2.

Referring now to the drawings, it is seen that the system for in-situ and on-line monitoring of fiber preform permeability variation for liquid composite molding (LCM) (which includes resin transfer molding, reaction injection molding, and resin infusion, etc.,), generally denoted by reference numeral 10, is comprised of a standard mold 12 for liquid composite molding having an upper mold section 14 and a lower mold section 16 (the lower mold section 16 being a one section design or as illustrated a two section design), having reject holes 18 and pin holes 20, wherein a fabric F or preform is loaded into the cavity within the mold 12 and the upper mold section 14 and lower mold section 16 are brought together in order to close the mold 12. Once the mold 12 is closed, a resin pump 22 pumps an appropriate resin into the closed mold 12 through at least one inlet port 24 which is fluid flow connected to the pump 22 via an appropriate conduit 26. A flow meter 28 is disposed between the inlet port 24 and the pump 22 so that the resin flow into the mold 12 can be monitored. Excess resin exits the mold through at least one outlet port 30.

Several holes 32 are located in the lower mold section 16. A pressure sensor 34 is attached to each hole 32 and each pressure sensor 34 is also connected to an appropriate data acquisition and processing device such as a computer 36, as is the flow meter 28. Advantageously, Micro Electro Mechanical Systems (MEMS) pressure sensors 34, such as those manufactured by Lucas NovaSensor Company of Fremont Calif., as well as others, are used due to their relatively low cost and high sensitivity and long term stability compared to other pressure sensors. An appropriate external excitation and offset circuit (not illustrated) can be constructed using operation amplifiers and resistors and be connected to each pressure sensor 34. Alternately, MEMS pressure sensors with built-in amplification circuits can be used such that the external excitation and offset circuits can be eliminated. Additionally, the MEMS pressure sensor 34 requires a relatively small hole 32 in the lower mold section 16. thereby allowing a robust density of holes 32 and pressure sensors 34 to populate the mold 12.

Figure 6:
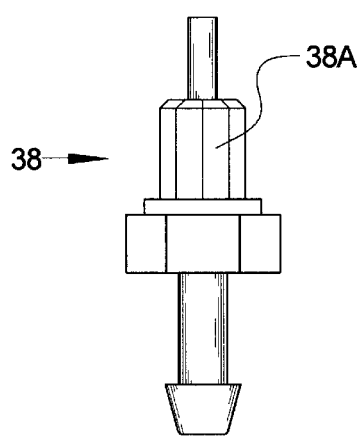
FIG. 6 is a side view of the first type of adapter used with the system of the present invention.
Figure 7:
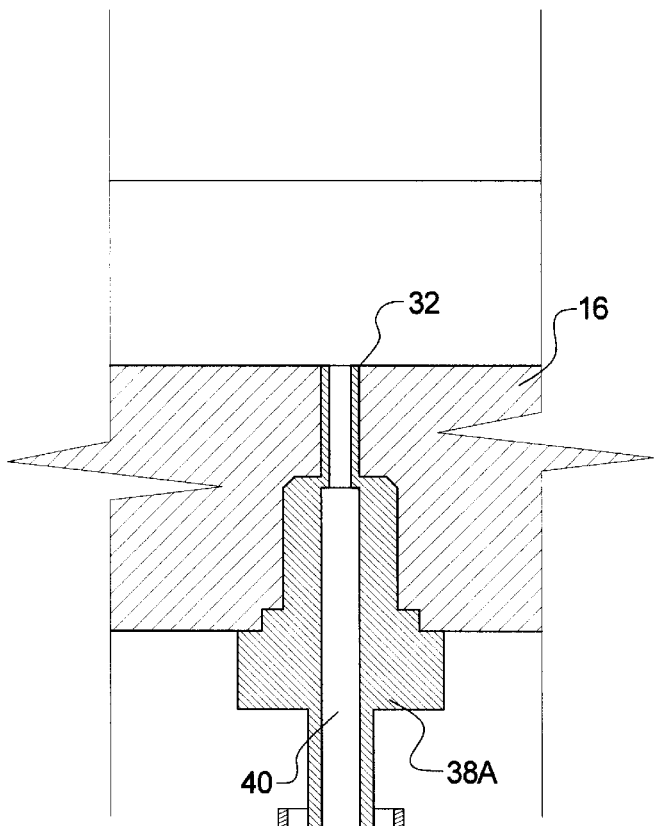
FIG. 7 is a sectioned view of the first type of adapter received within a hole in the lower mold section.
Figure 8:
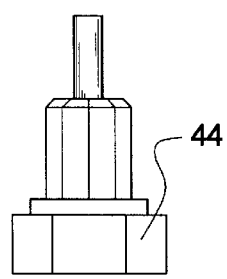
FIG. 8 is a side view of the sealing plug used with the system of the present invention.
Figure 9:
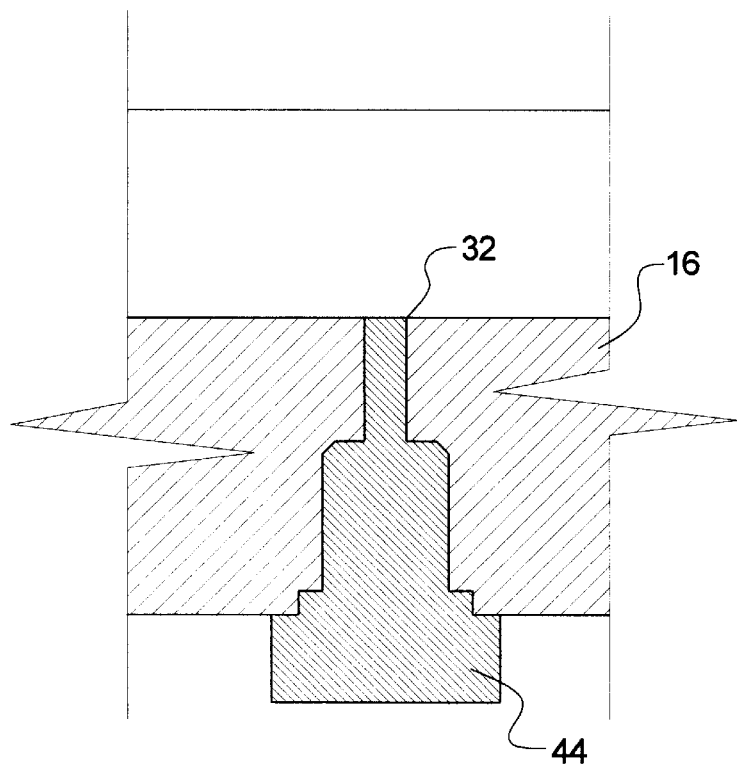
FIG. 9 is a sectioned view of the sealing plug received within a hole in the lower mold section.
Figure 10:
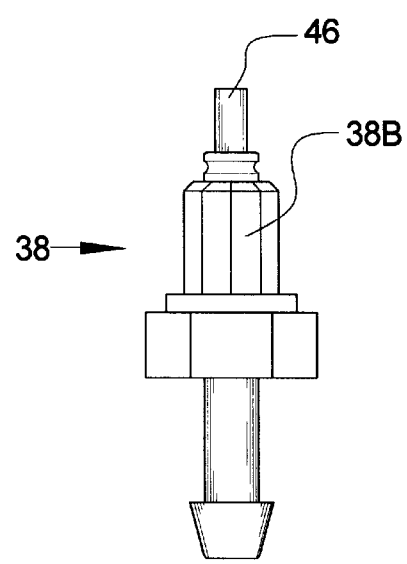
FIG. 10 is a side view of the second type of adapter used with the system of the present invention.
Figure 11:
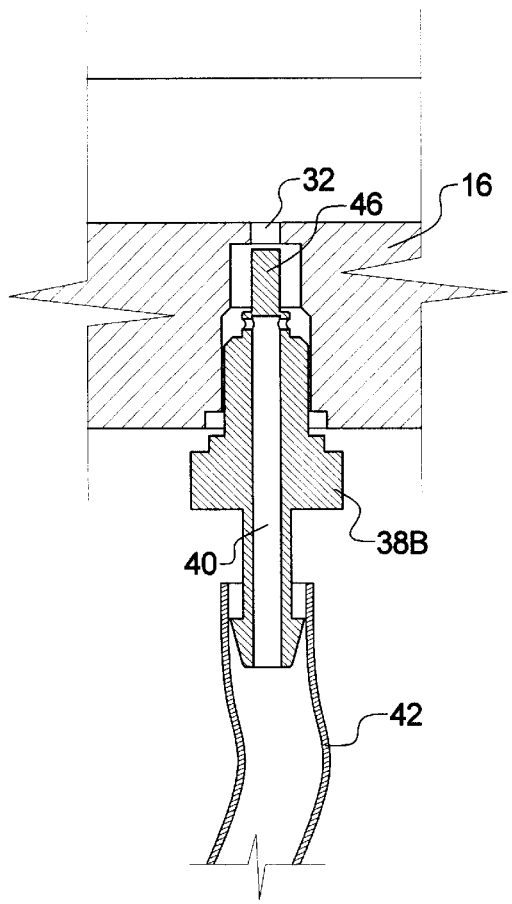
FIG. 11 is a sectioned view of the second type of adapter received within a hole in the lower mold section and in an open position.
Figure 12:
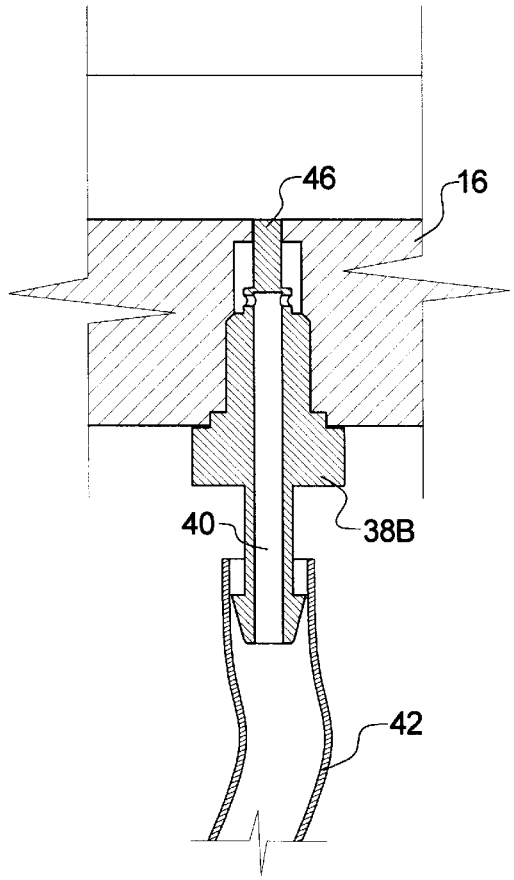
FIG. 12 is a sectioned view of the second type of adapter received within a hole in the lower mold section and in a closed position.

The pressure sensor 34 can be attached directly to its respective hole 32, however, it is more advantageous to connect the pressure sensor 34 to the hole 32 via an adapter (reference number 38, although not in the figures being used to describe the adapter generally, reference number 38a being used to designate the first type of adapter and reference number 38b being used to reference the second type of adapter) wherein the adapter 38 is attached to the lower mold section 16 and any pressure measurements pass through a channel 40 within the adapter 38 to the pressure sensor 34 via a conduit 42. The use of an adapter 38 removes the pressure sensor 34 from direct contact with resin during the LCM process, which contact can damage or destroy a pressure sensor 34. The adapter 38 can be of the type illustrated in FIGS. 6 and 7, wherein a portion of the adapter 38a is inserted through the hole 32 such that the end of the adapter 38a is generally flush with the inner surface of the lower mold section 16. The conduit 42 connects the adapter 38a with the pressure sensor 34. When use of the pressure sensor 34 is not needed, the adapter 38a is removed from the hole 32 and a sealing plug 44 is inserted into the hole 32 in order to seal the hole 32. Alternately, the adapter 38 can be of the type illustrated in FIGS. 10–12 wherein the adapter 38b is operable between two positions. In FIG. 11, the adapter 38b is in an open position wherein the channel 40 is open and the pressure sensor 34 can take readings from the mold 12. Rotation of the adapter 38b causes it to move from the open position to the closed position, illustrated in FIG. 12, wherein a shank 46 on the adapter 38b is received within the upper section of the hole 32, the end of the shank 46 being generally flush with the inner surface of the lower mold section 16. Counterrotation of the adapter 38b will return the adapter 38b to its open position. The adapter 38 and the plug 44 are each made from an appropriate material such as engineering plastics such as PP and PET for LCM systems that have a curing temperature lower than about 120 degrees Celsius, while for systems that have a higher cure temperature, high performance plastics such as PPS or metal should be used to make the adapter 38 and the plug 44. By using an adapter 38 or plug 44 (described below), the adapter 38 or plug 44 is in contact with the resin and if one 38 or 44 should become damaged, or if a conduit 42 becomes clogged or otherwise inoperable, the damaged part (which is relatively less expensive than the pressure sensor 34) is discarded and replaced.

The inlet port 24 (at least one inlet port in a multiple inlet port 24 system) is connected to a source of pressurized gas 48, such as nitrogen ($N_2$) or compressed air. The pressurized gas source 48 can be connected to the same conduit 26 through which the resin pump 22 introduces the resin into the mold 12, via an appropriate valve 50.

In order to use the system for in-situ and on-line monitoring of preform layup process of liquid composite molding, the mold 12 is opened and the fabric or preform F is loaded into the cavity of the mold 12 in the usual way. The mold 12 is closed. Each plug 44 is removed from its respective hole 32 and is replaced with an adapter 38, the adapter 38 being connected to a pressure sensor 34 via a conduit 26. Alternately, if the second type of adapter 38b is used, the adapter 38b is rotated so as to place the adapter 38b into its open position. Thereafter the compressed gas source 48 is activated so as to introduce the compressed gas into the mold 12 through the inlet port 24. Each of the pressure sensors 34 takes a pressure reading and the data from the pressure sensor 34 is collected and processed. The collected data can be used to create a pressure profile, a contour profile, or can be processed in any other fashion desired by the user. The data, either in raw or processed form, is used by the user to determine if the preform F has any defects and/or if there is a misfit between the preform F and the mold 12 giving the user in-situ and on-line information regarding the preform layup, prior to actual liquid injection. If a defect or a misfit is detected, appropriate corrective action is taken. If there are no defects or misfits, then the LCM process continues. Accordingly, the adapters 38a are removed from their respective holes 32 and each is replaced with a plug 44 (or the adapter 38b is counterrotated to the closed position if the second type of adapter 38b is used). The compressed gas source 48 is deactivated and the valve 50 is articulated so that the resin flows from the resin pump 22 to the mold 12 in the usual way.

Figure 13:
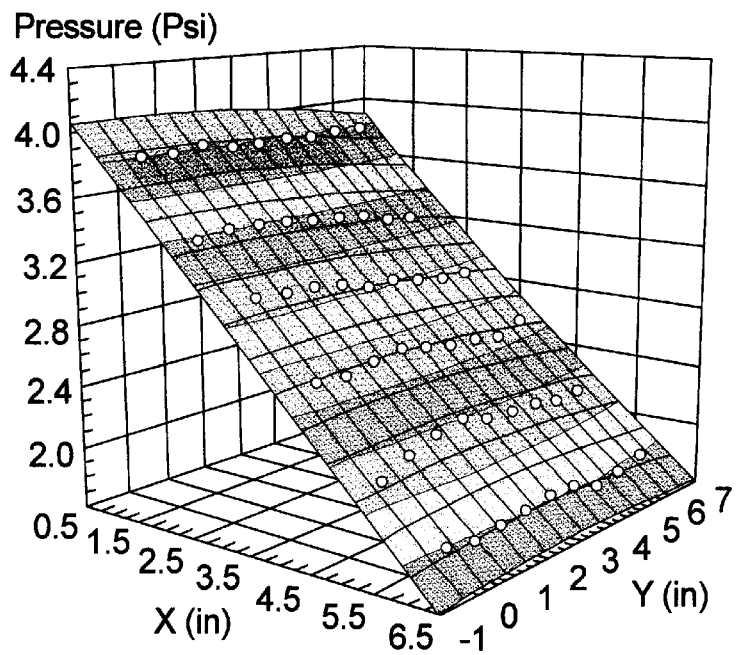
FIG. 13 is a graph of the measured pressure profile of the gas flow for a defect free and uniform permeability preform.
Figure 14:
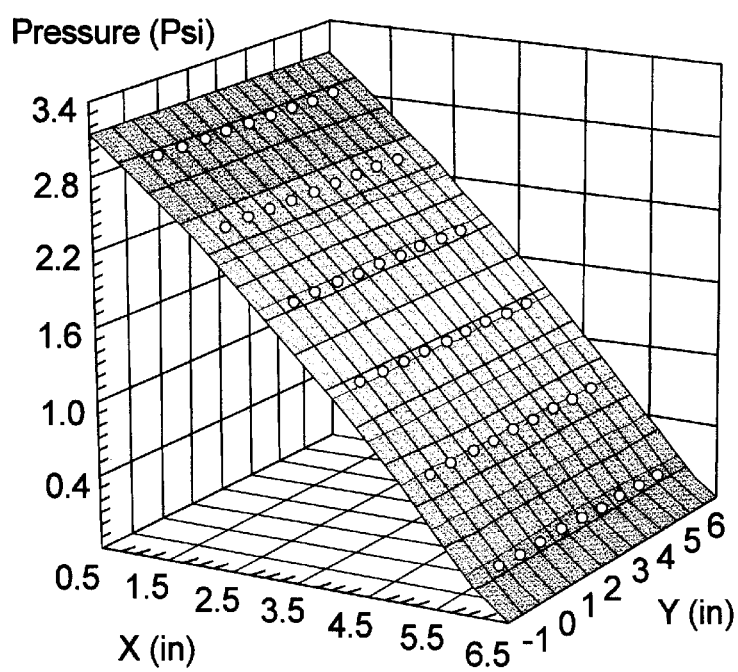
FIG. 14 is a graph of the simulated pressure profile of the gas flow for a defect free and uniform permeability preform.

In order to demonstrate use of the system of the present invention, a multiple layer knitted fabric having a fiber volume content of about 50 percent and a uniform gas permeability, the flow resistance of preform to the gas flow, in the cavity of about 1.82 E-6 cm$^2$ was prepared with accurate dimensions and clear edge cuts and was carefully loaded into the cavity of the mold 12. A theoretical pressure profile of the gas flow for this preform was calculated using a simulation tool developed at the Florida State University, Tallahassee, Fla., the profile is illustrated in FIG. 14 with each circle within the profile representing a point of calculated data. The pressure profile was measured using the system 10 of the present invention, the profile illustrated in FIG. 13, each circle in the profile representing a point of measured (pressure sensor 34) data.

Figure 15:
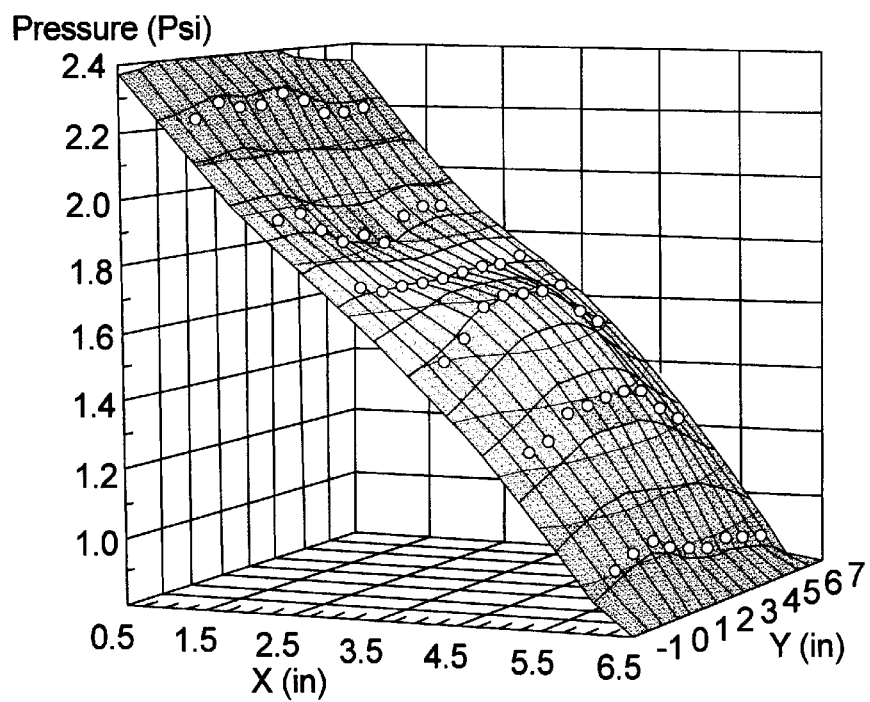
FIG. 15 is a graph of the measured pressure profile of the gas flow for a preform having a central cutout defect.
Figure 16:
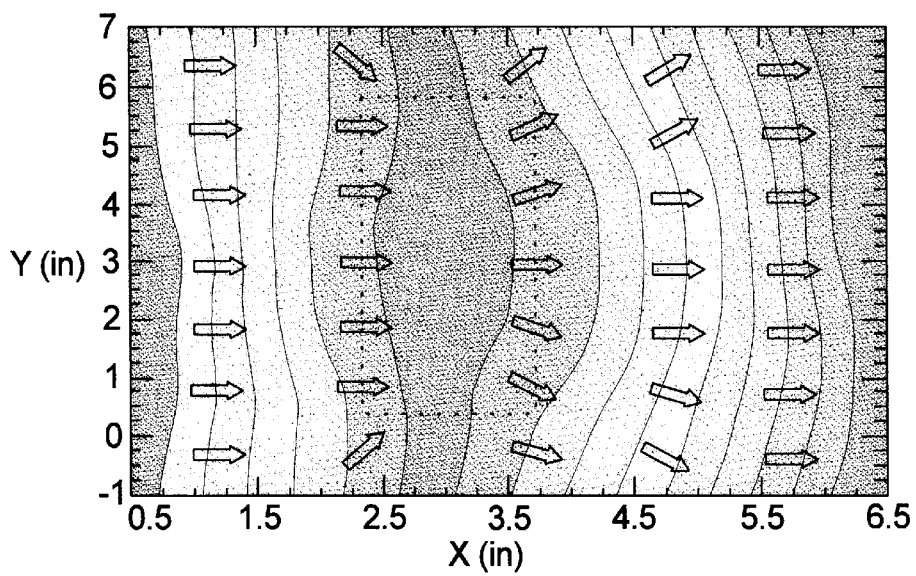
FIG. 16 is a contour profile of the graph of FIG. 15.

Thereafter, several layers of the preform F were cut out from a central portion of the preform, thereby reducing the fiber volume content of the preform at the cut out area to about 30 percent and the gas permeability to about 15.35 E-6 cm$^2$. The pressure profile was measured using the system 10, the profile is illustrated in FIG. 15, each circle in the profile representing a point of measured (pressure sensor 34) data, while the contour of the pressure profile is illustrated in FIG. 16 wherein the arrows represent flow direction and the dotted lines delimit the cut out area. The pressure profile and the contour profile each show a gas permeability variation due to the cut out area and allow corrective action to be taken.

Figure 17:
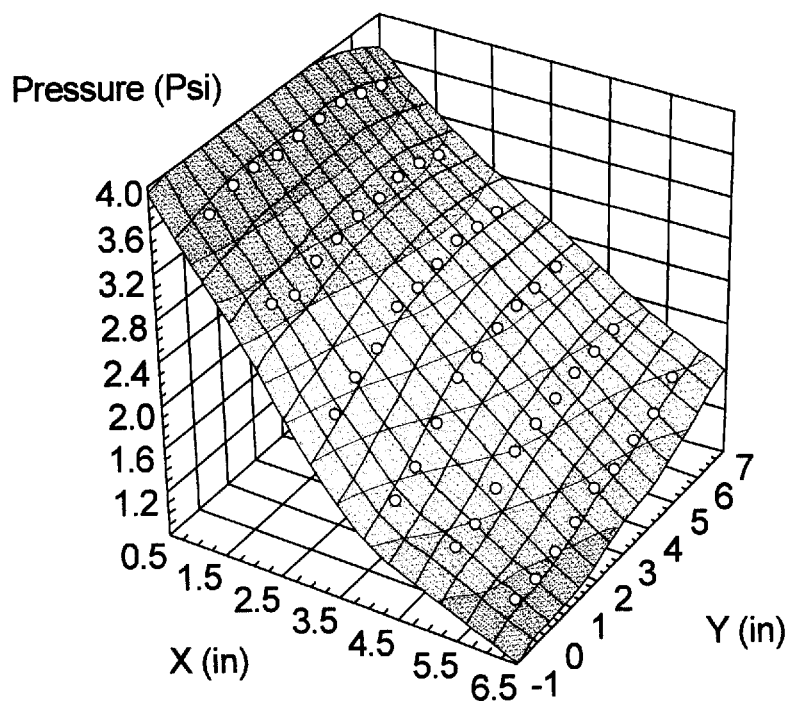
FIG. 17 is a graph of the measured pressure profile of the gas flow for a preform having a race tracking defect.
Figure 18:
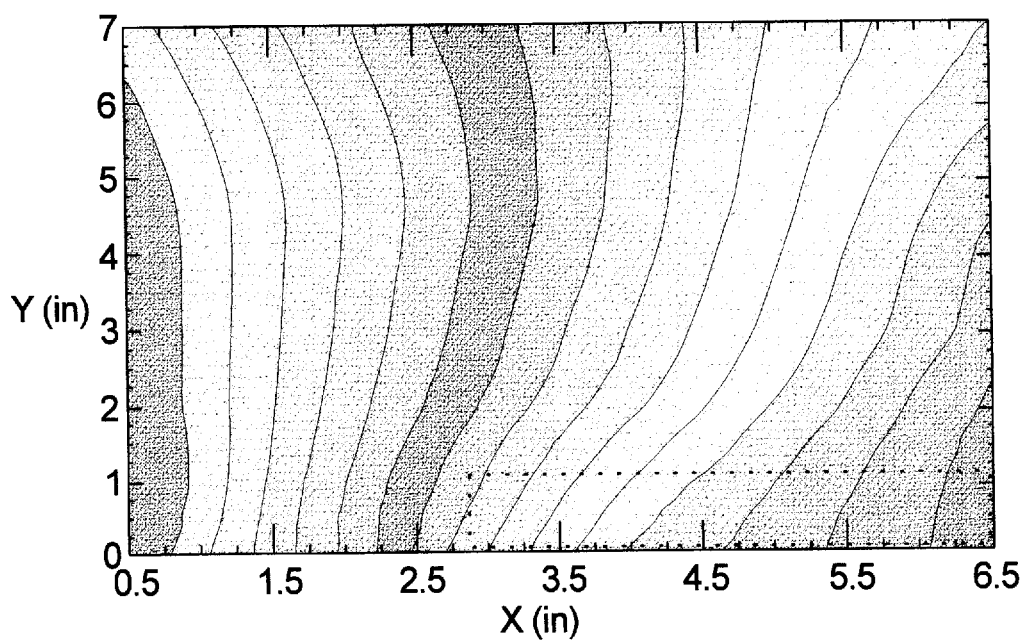
FIG. 18 is a contour profile of the graph of FIG. 16.

In another example, race tracking was induced by a misfit between the preform F and the mold 12. Several layers were cut out along one edge of the preform to simulate the low flow resistance channel induced by misfit between the preform F and the mold 12. The pressure profile was measured using the system 10, the profile is illustrated in FIG. 17, each circle in the profile representing a point of measured (pressure sensor 34) data, while the contour of the pressure profile is illustrated in FIG. 18 wherein the arrows represent flow direction and the dotted lines delimit the cut out area. The pressure profile and the contour profile each show a gas permeability variation due to the cut out area (simulating preform and mold misfit) and allow corrective action to be taken.

Furthermore, the detected gas permeability correlated with the liquid permeability variation for the same preform used in an LCM process Therefore, the in-situ and on-line detection of permeability variation of a preform for an LCM process can be conducted before actual liquid resin injection.

While the invention has been particularly shown and described with reference to an embodiment thereof, it will be appreciated by those skilled in the art that various changes in form and detail may be made without departing from the spirit and scope of the invention.

We claim:

1. A measurement system comprising:
   a mold having an upper section and a lower section forming a cavity therebetween and having an inlet port and an outlet port;
   a plurality of openings located within the lower section
   a plurality of pressure sensors, each attached to a respective one of the plurality of openings via an adapter; and
   a source of compressed gas, fluid flow connected to the inlet port.

2. The measurement system as in claim 1 wherein the pressurized gas is nitrogen.

3. The measurement system as in claim 1 wherein the adapter is operable between an open position wherein fluid flow communication between the pressure sensor and its respective opening is present and a closed position wherein fluid flow communication between the pressure sensor and its respective opening is absent.

4. The measurement system as in claim 1 wherein each pressure sensor is a MEMS pressure sensor.

5. The measurement system as in claim 1 wherein each pressure sensor is connected to a data acquisition and processing device.

6. The measurement system as in claim 5 wherein the data acquisition and processing device is a computer.

7. The measurement system as in claim 1 further comprising a reject hole located within the mold.

8. The measurement system as in claim 1 further comprising a pin hole located within the mold.

9. The measurement system as in claim 1 further comprising a flow meter connected with the inlet port.

10. The measurement system as in claim 9 wherein each pressure sensor and the flow meter are each connected to a data acquisition and processing device.

11. The measurement system as in claim 10 wherein the data acquisition and processing device is a computer.

12. The measurement system as in claim 1 further comprising a resin pump connected to the inlet port.

13. The measurement system as in claim 12 further comprising a flow meter connected with the inlet port.

14. The measurement system as in claim 13 wherein each pressure sensor and the flow meter are each connected to a data acquisition and processing device.

15. The measurement system as in claim 14 wherein the data acquisition and processing device is a computer.

16. A method for monitoring the permeability of a preform comprising the steps of:
   providing a mold having an upper section and a lower section forming a cavity therebetween and having an inlet port and an outlet port;
   placing a liquid composite molding preform into the cavity;
   providing a plurality of openings located within the lower section;

providing a plurality of pressure sensors, each attached to a respective one of the plurality of openings;

providing a source of compressed gas, fluid flow connected to the inlet port;

activating the source of pressurized gas; and taking readings from the plurality of pressure sensors prior to the introduction of resin into the mold.

17. The method as in claim 16 wherein the pressurized gas is nitrogen.

18. The method as in claim 16 wherein each pressure sensor is attached to its respective opening via an adapter.

19. The method as in claim 18 wherein the adapter is operable between an open position wherein fluid flow communication between the pressure sensor and its respective opening is present and a closed position wherein fluid flow communication between the pressure sensor and its respective opening is absent.

20. The method as in claim 16 wherein each pressure sensor is a MEMS pressure sensor.

21. The method as in claim 16 wherein the readings of the plurality of the pressure sensors are taken by a data acquisition and processing device.

22. The method as in claim 21 wherein the data acquisition and processing device is a computer.

23. The method as in claim 16 further comprising the step of providing a reject hole located within the mold.

24. The method as in claim 16 further comprising the step of providing a pin hole located within the mold;

taking the readings of the flow meter.

25. The method as in claim 16 further comprising the steps of:

providing a flow meter connected with the inlet port; and taking the readings of the flow meter.

26. The method as in claim 25 wherein readings from each of the plurality of pressure sensor and the flow meter are taken by a data acquisition and processing device.

27. The method as in claim 26 wherein the data acquisition and processing device is a computer.

28. The method as in claim 16 further comprising a resin pump fluid flow connected to the inlet port.

29. The method as in claim 28 further comprising the steps of:

deactivating the source of pressurized gas;

removing each of the pressure sensors from its respective opening;

providing a plurality of plugs each inserted within a respective one of the plurality of openings; and activating the resin pump.

30. The method as in claim 29 further comprising the steps of:

providing a flow meter connected with the inlet port; and taking the readings of the flow meter.

31. The method as in claim 30 wherein readings from each of the plurality of pressure sensor and the flow meter are taken by a data acquisition and processing device.

32. The method as in claim 31 wherein the data acquisition and processing device is a computer.

* * * * *